United States Patent [19]

Peck

[11] Patent Number: 4,798,826

[45] Date of Patent: Jan. 17, 1989

[54] BENZODIAZEPINE TRANQUILIZER COMBINATIONS AND THE USE THEREOF

[75] Inventor: Anthony W. Peck, Bromley, England

[73] Assignee: Burroughs Wellcome Co., Research Triangle Park, N.C.

[21] Appl. No.: 795,612

[22] Filed: Nov. 6, 1985

Related U.S. Application Data

[63] Continuation of Ser. No. 644,145, Aug. 24, 1984, Pat. No. 4,571,395, and a continuation of Ser. No. 226,256, Jan. 19, 1981, abandoned.

[30] Foreign Application Priority Data

Jan. 21, 1980 [GB] United Kingdom ................. 8001910

[51] Int. Cl.$^4$ .................... A61K 31/54; A61K 31/135
[52] U.S. Cl. ..................................... 514/221; 514/646
[58] Field of Search ................................ 514/222, 646

[56] References Cited

FOREIGN PATENT DOCUMENTS 1340032 12/1973 United Kingdom .

OTHER PUBLICATIONS

Chem. Abst. 91-32788H (1979).

Primary Examiner—Stanley J. Friedman
Attorney, Agent, or Firm—Donald Brown

[57] ABSTRACT

Combinations comprising (i) a drowsiness-inducing benzodiazepine tranquilliser and (ii) a compound selected from m-chloro-α-t-butylaminopropiophenone, m-fluoro-α-t-butylaminopropiophenone and the pharmacologically and pharmaceutically acceptable acid addition salts thereof, pharmaceutical formulations comprising a said combination toegther with an acceptable carrier therefor, the preparation of such combinations and formulations, and the concomitant use in human medicine of such a benzodiazepine compound and a said propiophenone or salt thereof.

Concomitant administration of a said propiophenone or salt thereof prevents the functional impairment and drowsiness in man which follow the administration of such a benzodiazepine compound.

5 Claims, No Drawings

BENZODIAZEPINE TRANQUILIZER COMBINATIONS AND THE USE THEREOF

This is a continuation of application Ser. No. 644,145, filed Aug. 24, 1984, issued as U.S. Pat. No. 4,571,395, and a continuation of Ser. No. 226,256, filed Jan. 19, 1981, now abandoned.

This invention relates to combinations of an m-halo-α-t-butylaminopropiophenone or a pharmacologically and pharmaceutically acceptable acid addition salt thereof with a benzodiazepine tranquilliser, to pharmaceutical formulations comprising such a combination, to the preparation of such combinations and formulations, and to the concomitant use in human medicine of a said propiophenone or salt thereof and such a benzodiazepine compound.

m-Chloro-α-t-butylaminopropiophenone, m-fluoro-α-t-butylaminopropiophenone and the pharmacologically and pharmaceutically acceptable acid addition salts thereof are known to exhibit antidepressant properties when tested by standard techniques, see for example United Kingdom patent specification no. 1 340 032 which is incorporated herein by reference thereto.

It is also known that a number of compounds of the benzodiazepine type have been proposed for use in human medicine as tranquillisers (anxiolytics) for the treatment inter alia of anxiety and have to a varying degree found clinical acceptance. Certain of such compounds however give rise to drowsiness and functional impairment, side effects often unwanted as limiting the performance of the recipient (see for example The Pharmacological Basis of Therapeutics, Goodman L.S. and Gilman A. eds., Macmillan Publishing Co., Inc., fifth edition (1975) at pages 187 to 193, and Martindale: The Extra Pharmacopoeia, Wade A. ed., The Pharmaceutical Press, twenty-seventh edition (1977) at pages 1515 to 1570, all of which is incorporated herein by reference thereto). The drowsiness-inducing benzodiazepine tranquillisers include the following:

7-bromo-1,3-dihydro-5-(2-pyridinyl)-2H-1,4-benzodiazepin-2-one (bromazepam);
7-chloro-N-methyl-5-phenyl-3H-1,4-benzodiazepin-2-amine 4-oxide (chlordiazepoxide) and salts thereof;
7-chloro-2,3-dihydro-2,2-dihydroxy-5-phenyl-1H-1,4-benzodiazepine-3-carboxylic acid (clorazepate) and salts thereof;
7-chloro-1,3-dihydro-1-methyl-5-phenyl-2H-1,4-benzodiazepin-2-one (diazepam);
7-chloro-5-(o-chlorophenyl)-1,3-dihydro-3-hydroxy-2H-1,4-benzodiazepin-2-one (lorazepam);
7-chloro-2,3-dihydro-1-methyl-5-phenyl-1H-1,4-benzodiazepine (medazepam) and salts thereof;
7-chloro-1,3-dihydro-3-hydroxy-5-phenyl-2H-1,4-benzodiazepin-2-one (oxazepam); and
7-chloro-1-(cyclopropylmethyl)-1,3-dihydro-5-phenyl-2H-1, 4-benzodiazepin-2-one (prazepam).

It has now been found that the functional impairment and drowsiness in man which follow the administration of a drowsiness-inducing benzodiazepine tranquilliser may be prevented by the concomitant administration of a compound selected from m-chloro-α-t-butylaminopropiophenone, m-fluoro-α-t-butylaminopropiophenone and the pharmacologically and pharmaceutically acceptable acid addition salts thereof. Suitable indications for the administration of the two agents in this manner include (a) the treatment in man of mixed anxiety and depression, in particular in situations where functional impairment or drowsiness is undesirable, and
(b) the treatment in man of anxiety in situations where functional impairment or drowsiness is undesirable.

The propiophenone and benzodiazepine compounds may each be administered to the human recipient by any suitable route but preferably by a route selected from oral and parenteral (including subcutaneous, intradermal, intramuscular and intravenous). Desirably the same route is used for both compounds.

The size of dose required of the propiophenone and benzodiazepine compounds respectively will depend upon a number of factors including the identity of the recipient, the severity and precise nature of the condition to be treated and the route of administration and will ultimately be at the discretion of the attendant physician.

A dose of the propiophenone compound effective in preventing the functional impairment and drowsiness induced by the benzodiazepine compound will generally lie in the range 15 to 600 mg per day and more often in the range 18.75 to 450 mg per day. The desired dose is preferably presented as between two and four sub-doses administered at appropriate intervals throughout the day, thus where three subdoses are employed each will generally lie in the range 5 to 200 mg and more often in the range 6.25 to 150 mg. For an adult human a suitable daily dose will generally lie in the range 60 to 600 mg and more often in the range 75 to 450 mg; where this is presented as three sub-doses each will thus generally lie in the range 20 to 200 mg and more often in the range 25 to 150 mg. A suitable daily dose for a child will generally be of the order of 25 to 50% of that for an adult and thus will generally lie in the range 15 to 300 mg and more often in the range 18.75 to 225 mg; where this is presented as three sub-doses each will generally lie in the range 5 to 100 mg and more often in the range 6.25 to 75 mg.

Where the propiophenone compound is administered by the oral route an effective dose will generally lie in the range 60 to 600 mg per day conveniently presented as three sub-doses each in the range 20 to 200 mg, and will more often lie in the range 75 to 450 mg per day conveniently presented as three sub-doses each in the range 25 to 150 mg. A daily oral dose for an adult human will generally lie in the range 225 to 500 mg, conveniently three sub-doses each in the range 75 to 200 mg, and more often in the range 300 to 450 mg conveniently as three sub-doses each in the range 100 to 150 mg. For a child a daily oral dose will generally lie in the range 60 to 300 mg, conveniently three sub-doses each in the range 20 to 100 mg, and more often in the range 75 to 225 mg conveniently as three sub-doses each in the range 25 to 75 mg.

Where the propiophenone compound is administered by the parenteral (subcutaneous, intradermal, intramuscular or intravenous) route an effective dose will generally lie in the range 15 to 375 mg per day conveniently presented as three sub-doses each in the range 5 to 125 mg, and will more often lie in the range 18.75 to 300 mg per day conveniently presented as three sub-doses each in the range 6.25 to 100 mg. A daily parenteral dose for an adult human will generally lie in the range 60 to 375 mg conveniently three sub-doses each in the range 20 to 125 mg, and more often in the range 75 to 300 mg conveniently as three sub-doses each in the range 25 to 100 mg. For a child a daily parenteral dose will generally lie in the range 15 to 180 mg, conveniently three sub-doses each in the range 5 to 60 mg, and more often in the range 18.75 to 150 mg conveniently as three sub-doses each in the range 6.25 to 50 mg.

Antidepressant-effective daily doses and subdoses of the propiophenone compound will generally lie within the appropriate ranges indicated in the foregoing as "more often" effective in preventing the functional impairment and drowsiness.

Full information as to doses and administration regimes in respect of the benzodiazepine compounds may be found in the literature, for example the ABPI Data Sheet Compendium 1979–80 published by Pharmind Publications Limited and the Physicians' Desk Reference, 33rd edition (1979) published by Medical Economics Company all of which is incorporated herein by reference thereto.

The propiophenone and benzodiazepine compounds may be administered separately, either as the raw chemicals or as pharmaceutical formulations, but for general convenience it is desirable that the two compounds be presented together in combination. Preferably the compounds are presented as a combination formulation comprising (i) a compound selected from m-chloro-α-t-butylaminopropiophenone, m-fluoro-α-t-butylaminopropiophenone and the pharmacologically and pharmaceutically acceptable acid addition salts thereof, and (ii) a drowsiness-inducing benzodiazepine tranquilliser, together with one or more acceptable carriers therefor and optionally other therapeutic ingredients. The carrier(s) must be 'acceptable' in the sense of being compatible with the other ingredients of the formulation and not deleterious to the recipient thereof.

The formulations include those suitable for oral or parenteral (including subcutaneous, intradermal, intramuscular and intravenous) administration although the most suitable route may depend upon for example the condition of the recipient. The formulations may conveniently be presented in unit dosage form and may be prepared by any of the methods well known in the art of pharmacy. All methods include the step of bringing into association the propiophenone and benzodiazepine compounds (the active ingredients) with the carrier which constitutes one or more accessory ingredients. In general the formulations are prepared by uniformly and intimately bringing into association the active ingredients with liquid carriers or finely divided solid carriers or both, and then, if necessary, shaping the product into the desired formulation.

Formulations of the present invention suitable for oral administration may be presented as discrete units such as capsules, cachets or tablets each containing a predetermined amount of each active ingredient; as a powder or granules; as a solution or a suspension in an aqueous liquid or a non-aqueous liquid; or as an oil-in-water liquid emulsion or a water-in-oil liquid emulsion. The active ingredients may also be presented as a bolus, electuary or paste.

A tablet may be made by compression or moulding, optionally with one or more accessory ingredients. Compressed tablets may be prepared by compressing in a suitable machine the active ingredients in a free-flowing form such as a powder or granules, optionally mixed with a binder, lubricant, inert diluent, lubricating, surface active or dispersing agent. Moulded tablets may be made by moulding in a suitable machine a mixture of the powdered compounds moistened with an inert liquid diluent. The tablets may optionally be coated or scored and may be formulated so as to provide slow or controlled release of the active ingredients therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

It should be understood that in addition to the ingredients particularly mentioned above the formulations of this invention may include other agents conventional in the art having regard to the type of formulation in question, for example those suitable for oral administration may include flavouring agents.

Preferred unit dosage formulations are those containing a daily dose or unit daily sub-dose of each of the two active ingredients, or an appropriate fraction thereof.

As regards the propiophenone ingredient, suitable amounts for presentation as unit dosage formulations include the following:
(a) for oral administration: 25 mg, 50 mg, 75 mg, 100 mg and 150 mg;
(b) for parenteral administration: 6.25 mg, 12.5 mg, 25 mg, 50 mg and 100 mg.

As regards the benzodiazepine ingredient, suitable amounts for presentation as unit dosage formulations include the following:
(a) for oral administration:
chlordiazepoxide and salts thereof: 5 mg, 10 mg and 25 mg;
clorazepate and salts thereof: 3.75 mg, 7.5 mg, 11.25 mg, 15 mg and 22.5 mg;
diazepam: 2 mg, 5 mg and 10 mg;
lorazepam: 0.5 mg, 1 mg and 2 mg;
medazepam and salts thereof: 5 mg and 10 mg;
oxazepam: 10 mg, 15 mg and 30 mg; and
prazepam: 10 mg;
(b) for parenteral administration:
chlordiazepoxide and salts thereof: 100 mg;
diazepam: 10 mg and 20 mg; and
lorazepam; 4 mg.

It will be appreciated that where the benzodiazepine compound is administered or formulated in the form of a salt the said salt should be pharmacologically and pharmaceutically acceptable.

The propiophenone compound is preferably selected from m-chloro-α-t-butylaminopropiophenone and the pharmacologically and pharmaceutically acceptable acid addition salts thereof and is more preferably one of the said salts thereof.

Especially preferred amongst the propiophenone compounds is m-chloro-α-t-butylaminopropiophenone hydrochloride.

The benzodiazepine compound is preferably selected from 7-chloro-N-methyl-5-phenyl-3H-1,4-benzodiazepin-2-amine 4-oxide (chlordiazepoxide) and salts thereof, in particular the hydrochloride salt, and 7-chloro-1,3-dihydro-1-methyl-5-phenyl-2H-1,4-benzodiazepin-2-one (diazepam).

It will be understood from the foregoing description that this invention may comprise any novel feature described herein, principally but not exclusively for example:

(a) a combination comprising (i) a drowsiness-inducing amount of a drowsiness-inducing benzodiazepine tranquilliser and (ii) a compound selected from m-chloro-α-t-butylaminopropiophenone, m-fluoro-α-t-butylaminopropiophenone and the pharmacologically and pharmaceutically acceptable acid addition salts thereof in an amount effective to prevent the drowsiness induced by the said tranquilliser;

(b) a pharmaceutical formulation comprising (i) a drowsiness-inducing amount of a drowsiness-inducing benzodiazepine tranquilliser and (ii) a compound selected from m-chloro-α-t-butylaminopropiophenone, m-fluoro-α-t-butylaminopropiophenone and the pharmacologically and pharmaceutically acceptable acid addition salts thereof in an amount effective to prevent the drowsiness induced by the said tranquilliser, together with an acceptable carrier therefor;

(c) a formulation according to (b) wherein the propiophenone is selected from m-chloro-α-t-butylaminopropiophenone and the pharmacologically and pharmaceutically acceptable acid addition salts thereof:

(d) a formulation according to (b) wherein the propiophenone is a pharmacologically and pharmaceutically acceptable acid addition salt of m-chloro-α-t-butylaminopropiophenone;

(e) a formulation according to (b) wherein the propiophenone is m-chloro-α-t-butylaminopropiophenone hydrochloride;

(f) a formulation according to any of (b) to (e) wherein the tranquilliser is selected from
bromazepam;
chlordiazepoxide and the pharmacologically and pharmaceutically acceptable salts thereof;
clorazepate and the pharmacologically and pharmaceutically acceptable salts thereof;
diazepam;
lorazepam;
medazepam and the pharmacologically and pharmaceutically acceptable salts thereof;
oxazepam; and
prazepam;

(g) a formulation according to any of (b) to (e) wherein the tranquilliser is selected from chlordiazepoxide and the pharmacologically and pharmaceutically acceptable salts thereof;

(h) a formulation according to any of (b) to (e) wherein the tranquilliser is chlordiazepoxide;

(i) a formulation according to any of (b) to (e) wherein the tranquilliser is chlordiazepoxide hydrochloride;

(j) a formulation according to any of (b) to (e) wherein the tranquilliser is diazepam;

(k) a formulation according to any of (b) to (j) suitable for oral administration;

(l) a formulation according to any of (b) to (j) suitable for parenteral administration;

(m) a combination or formulation respectively according to (a) and any of (b) to (l) wherein the propiophenone is present in an antidepressant-effective amount;

(n) a formulation according to any of (b) to (m) in unit dosage form comprising the propiophenone and the tranquilliser each in a non-toxic amount;

(o) a method for the preparation of a combination or formulation, as appropriate, according to any of (a) to (n) comprising admixture of the ingredients thereof and, if appropriate, shaping of the product;

(p) a method for preventing the function impairment and dowsiness in man which follow the administration of a drowsiness-inducing, non-toxic amount of a drowsiness-inducing benzodiazepine tranquilliser, comprising the concomitant administration of a compound selected from m-chloro-α-t-butylaminopropiophenone, m-fluoro-α-t-butylaminopropiophenone and the pharmacologically and pharmaceutically acceptable acid addition salts thereof in a non-toxic amount effective to prevent the functional impairment and drowsiness induced by the said tranquilliser; and (q) a method for the treatment in man of mixed anxiety and depression comprising the concomitant administration of (i) an anxiolytic-effective, non-toxic amount of a drowsiness-inducing benzodiazepine tranquilliser and (ii) an antidepressant-effective, non-toxic amount of a compound selected from m-chloro-α-t-butylainopropiophenone, m-fluoro-α-t-butylaminopropiophenone and the pharmacologically and pharmaceutically acceptable acid addition salts thereof.

The following examples are provided in illustration of the present invention and should not be construed as in any way constituting a limitation thereof.

EXAMPLE 1

Administration to man of
m-chloro-α-t-butylaminopropiophenone hydrochloride and diazepam 1) The effects of single oral doses of
a) m-chloro-α-t-butylaminopropiophenone hydrochloride (100 mg),
(b) diazepam (2.5 mg or 5 mg),
(c) the propiophenone compound of (a) (100 mg) plus diazepam (2.5 mg or 5 mg), and
(d) lactose dummy were separately examined in twelve healthy volunteers using a balanced cross over design and double blind conditions. Results were analysed by analysis of variance and values of $p < 0.005$ taken as significant.

(2) a significant reduction in signals detected in the Wilkinson vigilance test (*Prog. Clin. Psychol.*, 8, 28–43 (1968)) occurred after diazepam 5 mg and a similar trend occurred after diazepam 2.5 mg compared with dummy. Performance after the propiophenone compound 100 mg and after the propiophenone compound 100 mg plus diazepam 5mg did not differ from that after dummy.

Calculations indicated that diazepam reduced the subjects' ability to discriminate between signals and noise, rather than their willingness to report.

(3) Subjective effects, measured using visual analogue scales, showed that the subjects rated themselves significantly more drowsy, muzzy and dreamy after both diazepam 2.5 mg and diazepam 5 mg than after dummy. After the propiophenone compound 100 mg plus either diazepam 2.5 mg or diazepam 5 mg the ratings never differed from dummy on any dimension.

The subjective effects had largely disappeared by six hours after dosing.

(4) It was concluded that the propiophenone compound prevented the functional impairment and drowsiness seen after diazepam.

EXAMPLE 2

Pharmaceutical Formulations

Throughout the following the material referred to as Propiophenone Hydrochloride is m-chloro-α-t-butylaminopropiophenone hydrochloride.

(A) TABLETS (a) Propiophenone Hydrochloride plus Diazepam

|  | mg per tablet |
|---|---|
| Propiophenone Hydrochloride | 100 |
| Diazepam | 5 |
| Lactose | 200 |
| Starch | 60 |
| Methyl cellulose | 6 |
| Microcrystalline Cellulose | 100 |
| Magnesium Stearate | 4 |
|  | 475 |

Mix the Propiophenone Hydrochloride, Diazepam, Lactose, Starch and half of the Microcrystalline Cellulose. Granulate with a solution of the Methyl cellulose in water. Dry the granules. Mix in the rest of the Microcrystalline Cellulose and the Magnesium Stearate. Compress.

(b) Propiophenone Hydrochloride plus Chlordiazepoxide Hydrochloride

|  | mg per tablet |
|---|---|
| Propiophenone Hydrochloride | 100 |
| Chlordiazepoxide Hydrochloride | 10 |
| Lactose | 200 |
| Sodium Starch Glycollate | 20 |
| Polyvinylpyrrolidone | 6 |
| Microcrystalline Cellulose | 100 |
| Stearic Acid | 4 |
|  | 440 |

Mix the Propiophenone Hydrochloride, Chlordiazepoxide Hydrochloride, Lactose, Sodium Starch Glycollate and half the Microcrystalline Cellulose. Granulate with a solution of the Polyvinylpyrrolidone in 50% aqueous alcohol. Dry the granules. Mix in the rest of the Microcrystalline Cellulose and the Stearic Acid. Compress.

(B) CAPSULES (a) Propiophenone Hydrochloride plus Diazepam

|  | mg per capsule |
|---|---|
| Propiophenone Hydrochloride | 50 |
| Diazepam | 2 |
| Starch | 200 |
| Talc | 2 |
|  | 254 |

Mix the Propiophenone Hydrochloride, Diazepam, Starch and Talc. Fill into gelatin capsules.

(b) Propiophenone Hydrochloride plus Chlordiazepoxide Hydrochloride

|  | mg per capsule |
|---|---|
| Propiophenone Hydrochloride | 50 |
| Chlordiazepoxide Hydrochloride | 5 |
| Lactose | 150 |
| Starch | 30 |
| Gelatin | 2 |
| Magnesium Stearate | 2 |
|  | 239 |

Mix the Propiophenone Hydrochloride, Chlordiazepoxide Hydrochloride, Lactose and Starch. Granulate with a solution of Gelatin in 50% aqueous alcohol. Dry the granules. Mix in the Magnesium Stearate. Fill into gelatin capsules.

(C) SYRUP

|  |  |  |
|---|---|---|
| Propiophenone Hydrochloride | 12.5 | mg |
| Diazepam | 0.5 | mg |
| Sucrose | 3 500 | mg |
| Citric Acid | 25 | mg |
| Sodium Benzoate | 5 | mg |
| Methylhydroxybenzoate | 5 | mg |
| Glycerol | 500 | mg |
| Colour | 1.5 | mg |
| Flavour | 0.005 | ml |
| Purified water to | 5 | ml |

Dissolve the Methyl Hydroxybenzoate, Sodium Benzoate and Citric Acid in Purified Water. Add and dissolve the Sucrose and the Colour. Add and dissolve the Propiophenone Hydrochloride and Diazepam. Add the Glycerol and the flavour and make up to volume with Purified Water and mix. Filter to give a clear bright syrup.

(D) INJECTIONS (a) Propiophenone Hydrochloride plus Diazepam

|  |  |  |
|---|---|---|
| Propiophenone Hydrochloride | 25 | mg |
| Diazepam | 10 | mg |
| Propylene Glycol | 0.8 | ml |
| Alcohol | 0.2 | ml |
| Sodium Benzoate | 100 | mg |
| Benzoic Acid | 100 | mg |
| Benzyl Alcohol | 0.03 | ml |
| Water for Injection to | 2 | ml |

Dissolve the Propiophenone Hydrochloride and Diazepam in the Propylene Glycol and the Alcohol. Add the Benzyl Alcohol. Add and dissolve the Benzoic Acid and Sodium Benzoate. Make to volume with Water for Injection. Sterilise by filtration and fill under aseptic conditions into sterile vials or ampoules.

(b) Propiophenone Hydrochloride plus Chlordiazepoxide Hydrochloride
Vial 1

|  |  |
|---|---|
| Propiophenone Hydrochloride, Sterile | 100 mg |
| Chlordiazepoxide Hydrochloride, Sterile equivalent to base | 100 mg |

Mix the Propiophenone Hydrochloride, Sterile, and Chlordiazepoxide Hydrochloride, Sterile and fill into vials under aseptic conditions.
Vial 2 (diluent)

| | |
|---|---|
| Polysorbate 80 | 80 mg |
| Benzyl Alcohol | 0.03 ml |
| Propylene Glycol | 0.4 ml |
| Maleic Acid | 32 mg |
| Sodium Hydroxide | qs to pH 3 |
| Water for Injection to | 2 ml |

Mix the Polysorbate 80 and Propylene Glycol. Add the Benzyl Alcohol. Dissolve the Maleic Acid in 70% of the Water. Add this solution to the Polysorbate 80 solution. Adjust to pH 3 with the Sodium Hydroxide, make to volume with Water for Injection. Sterilise by filtration and fill under aseptic conditions into sterile vials or ampoules.

What we claim is:

1. A method for the treatment in humans of mixed anxiety and depression comprising the concomitant administration to a human of an effective anxiety treatment amount of a drowsiness-inducing benzodiazepine tranquillizer and m-chloro-α-t-butylamino propiophenone or a pharmaceutically acceptable salt thereof in an amount sufficient to prevent drowsiness caused by the tranquillizer, wherein the benzodiazepine tranquillizer is bromazepam; chlordiazepoxide and pharmacologically and pharmaceutically acceptable salts thereof; chlorazepate and pharmacologically and pharmaceutically acceptable salts thereof; diazepam; medazepam and pharmacologically and pharmaceutically acceptable salts thereof; oxazepam; or prazepam.

2. A method of claim 1 in which the hdyrochloride salt of m-chloro-α-t-butylaminopropiophenone is administered.

3. A pharmaceutical composition comprising in combination a tranquillizing amount of a drowsiness-inducing benzodiazepine tranquillizer other than lorazepan and an amount of m-chloro-α-t-butylaminopropiophenone or a pharmaceutically and pharmacologically acceptable salt thereof to prevent drowsiness cause by the tranquillizer, wherein the benzodiazepine tranquillizer is bromazepam; chlordiazepoxide and pharmacologically and pharmaceutically acceptable salts thereof; chlorazepate and pharmacologically and pharmaceutically acceptable salts thereof; diazepam; medazepam and pharmacologically and pharmaceutically acceptable salts thereof; oxazepam; or prazepam.

4. The composition of claim 3 wherein the benzodiazepine tranquillizer is bromazepam; chlordiazepoxide and pharmacologically and pharmaceutically acceptable salts thereof; chlorazepate and pharmacologically and pharmaceutically acceptable salts thereof; diazepam; medazepam and pharmacologically and pharmaceutically acceptable salts thereof; oxazepam; or prazepam.

5. The composition of claim 3 in which the hydrochloride salt of m-chloro-α-t-butylamino proprophenone* is combined with the tranquillizer

* * * * *